(12) United States Patent
Bremer et al.

(10) Patent No.: US 8,764,678 B2
(45) Date of Patent: Jul. 1, 2014

(54) PRESSURE SENSOR WITH AN INTERFEROMETRIC SENSOR AND AN IN-FIBER BRAGG GRATING REFERENCE SENSOR

(75) Inventors: Kort Bremer, Schneverdingen (DE); Gabriel Leen, Limerick (IE); Elfed Lewis, County Clare (IE); Brian J. Moss, County Limerick (IE); Steffen Lochmann, Dahlewitz (DE); Ingo Mueller, Ziesendorf (DE)

(73) Assignee: University of Limerick, Limerick (IE)

( * ) Notice: Subject to any disclaimer, the term of this patent is extended or adjusted under 35 U.S.C. 154(b) by 563 days.

(21) Appl. No.: 12/929,527

(22) Filed: Jan. 31, 2011

(65) Prior Publication Data
US 2011/0190640 A1    Aug. 4, 2011

Related U.S. Application Data

(60) Provisional application No. 61/282,389, filed on Feb. 1, 2010.

(51) Int. Cl.
*A61B 5/00* (2006.01)

(52) U.S. Cl.
USPC ........................................................ 600/561

(58) Field of Classification Search
USPC ................................................ 600/561, 587
See application file for complete search history.

(56) References Cited

U.S. PATENT DOCUMENTS 4,320,664 A * 3/1982 Rehn et al. ...................... 73/708
4,672,853 A * 6/1987 Hickox ............................ 73/708
4,788,521 A * 11/1988 Johnson ............................ 338/3
7,054,011 B2   5/2006 Zhu
2006/0133715 A1   6/2006 Belleville

OTHER PUBLICATIONS

D. C. Abeysinghe et al., "A Novel MEMS Pressure Sensor Fabricated on an Optical Fiber," IEEE Photonics Technology Letters, Sep. 2001, vol. 13, No. 9, pp. 993-995.

(Continued)

*Primary Examiner* — Max Hindenburg
(74) *Attorney, Agent, or Firm* — Jacobson Holman, PLLC.

(57) ABSTRACT

A pressure sensor (10 for medical applications comprises a silica optical fiber extrinsic Fabry-Perot interferometric (EFPI) pressure sensor (2) and an in-fiber Bragg grating (FBG, 3). The cavity of the EFPI pressure sensor (2) is formed by the end face of the FBG (3), a glass capillary (5) and a glass diaphragm (6). The glass diaphragm (6) is secured in place by a fusion splice (7) and the glass capillary (5) by a fusion splice (8). As illustrated, incident light is directed into the FBG 3 and there are reflections in the EFPI pressure sensor (2). Applied pressure causes a deflection of the glass diaphragm (6) and hence modulation of the EFPI sensor (2) cavity. The FBG (3) is used as a reference sensor to eliminate temperature cross-sensitivity of the EFPI pressure sensor (2). The EFPI cavity was fabricated using a 200 μm silica glass fiber, a 133/220 μm (inner/outer diameter) silica glass capillary and a standard telecommunication FBG. Initially, the end faces of the 200 μm silica glass fiber and the silica glass capillary were polished and both planar surfaces were spliced together using a fusion splicer. Then the silica glass capillary was cleaved 5 mm away form the capillary/200 μm fiber splice. After that, the FBG (3) was inserted into the silica glass capillary (5) and both elements were bonded together using the fusion splicer again.

9 Claims, 7 Drawing Sheets

(56) References Cited

OTHER PUBLICATIONS

Y. Zhu et al., "High-Temperature Fiber-Tip Pressure Sensor," Journal of Lightwave Technology, Feb. 2006, vol. 24, No. 2, pp. 861-869.
Mario di Giovanni, "Flat and corrugated diaphragm design handbook. Mechanical Engineering; 11," 1982, Marcel Dekker, Inc.
A. D. Kersey et al., "Fiber Grating Sensors," Journal of Lightwave Technology, Aug. 1997, vol. 15, No. 8, pp. 1442-1463.
F. Shen et al., "Frequency-estimation-based signal-processing algorithm for white-light optical fiber Fabry-Perot interferometers," Applied Optics, Sep. 1, 2005, vol. 44, No. 25, pp. 5206-5214.
W. Li et al., "Wavelength multiplexing of microelectromechanical system pressure and temperature sensors using fiber Bragg gratings and arrayed waveguide gratings," Optical Engineering, Feb. 2003, vol. 42, No. 2, pp. 431-438.
E. Cibula et al., "Miniature fiber-optic pressure sensor with a polymer diaphragm," Applied Optics, May 10, 2005, vol. 44, No. 14, pp. 2736-2744.
J. Xu et al., "Miniature all-silica fiber optic pressure and acoustic sensors," Optics Letters, Dec. 15, 2005, vol. 30, No. 24, pp. 3269-3271.
X. Wang et al., "All-fused-silica miniature optical fiber tip pressure sensor," Optics Letters, Apr. 1, 2006, vol. 31, No. 7, pp. 885-887.
X. Wang et al., "An Optical Fiber Tip Pressure Sensor for Medical Applications," 2005 Quantum Electronics and Laser Science Conference (QELS), pp. 916-918.
D. Donlagic et al., "All-fiber high-sensitivity pressure sensor with $SiO_2$ diaphragm," Optics Letters, Aug. 15, 2005, vol. 30, No. 16, pp. 2071-2073.

Y. Zhu et al., "Miniature Fiber-Optic Pressure Sensor," IEEE Photonics Technology Letters, Feb. 2005, vol. 17, No. 2, pp. 447-449.
G.C. Hill et al., "SU-8 MEMS Fabry-Perot pressure sensor," Sensors and Actuators A, 2007, vol. 138, pp. 52-62.
R. A. Wolthuis et al., "Development of Medical Pressure and Temperature Sensors Employing Optical Spectrum Modulation," IEEE Transactions on Biomedical Engineering, Oct. 1991, vol. 38, No. 10, pp. 974-981.
R. Wolthuis et al., "Development of a Dual Function Sensor System for Measuring Pressure and Temperature at the Tip of a Single Optical Fiber," IEEE Transactions on Biomedical Engineering, Mar. 1993, vol. 40, No. 3, pp. 298-302.
E. Cibula et al., "62.5: Miniature Fiber Optic Pressure Sensor for Medical Applications," IEEE Sensors, Hyatt Orlando, FL, USA, Jun. 12-14, 2002, pp. 711-714.
K. Bremer et al., "An optical fiber micro pressure sensor with high temperature immunity," $5^{th}$ International Symposium on Automatic Control, Sep. 18-19, 2008, Wismar, Germany.
K. Bremer et al., "Micro fiber optic pressure sensor based on a glass capillary and a glass diaphragm," First Asian Conference on e-Business and Telecommunications, Feb. 9-10, 2009, Changhua City, Taiwan.
K. Bremer et al., "Fabrication of a high-temperature-resistance optical fiber micro pressure sensor," IEEE Sixth International Multi-Conference on System, Signal and Devices (SSD'09), Mar. 23-26, 2009, Djerba, Tunisia.

\* cited by examiner

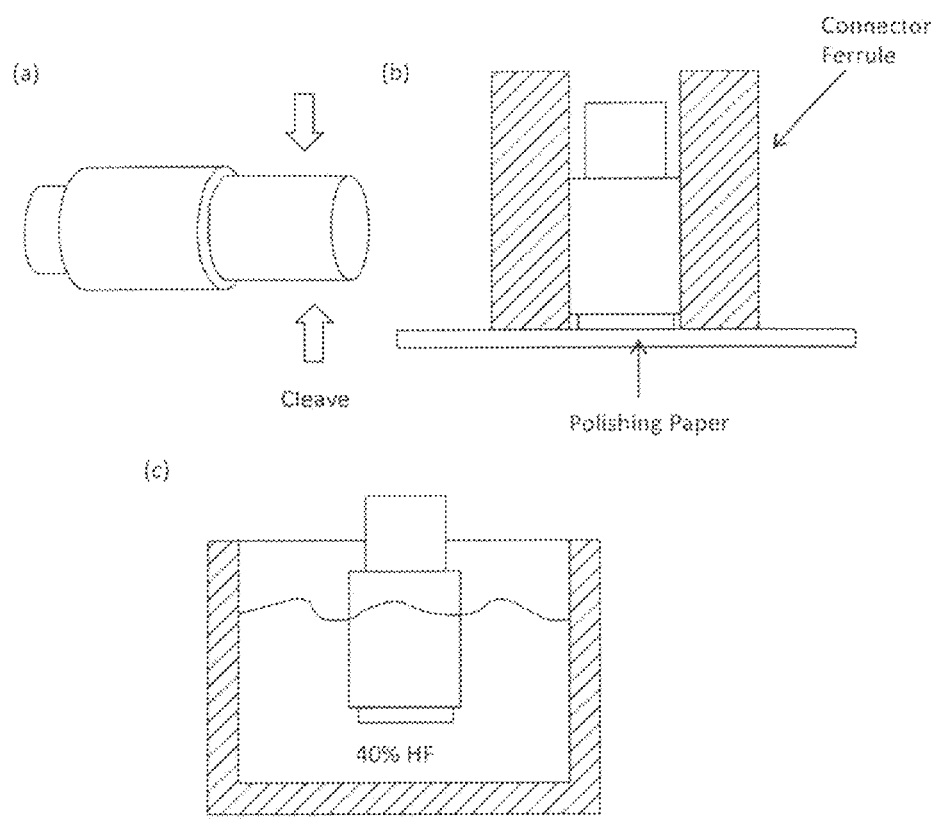
Fig. 3
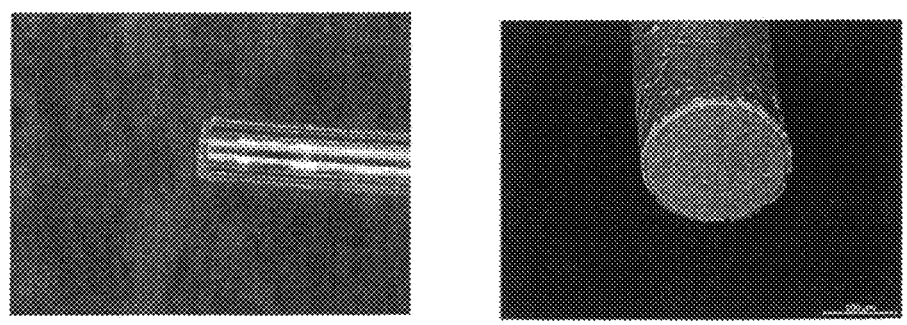
Fig. 4: Pressure sensor before etching
Fig. 5: Glass diaphragm surface after etching

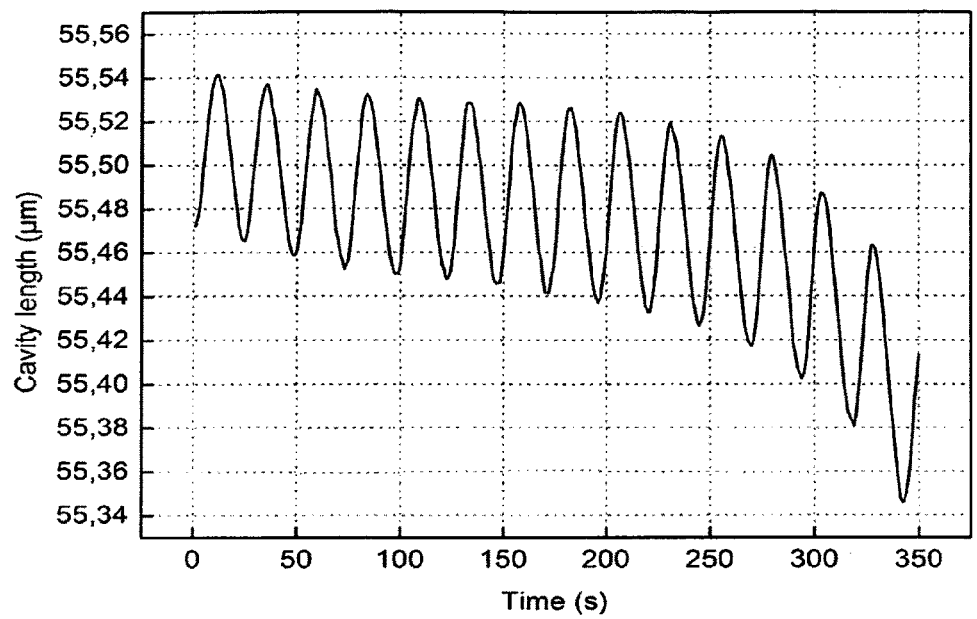
Fig. 6: Change of EFPI cavity length during etching
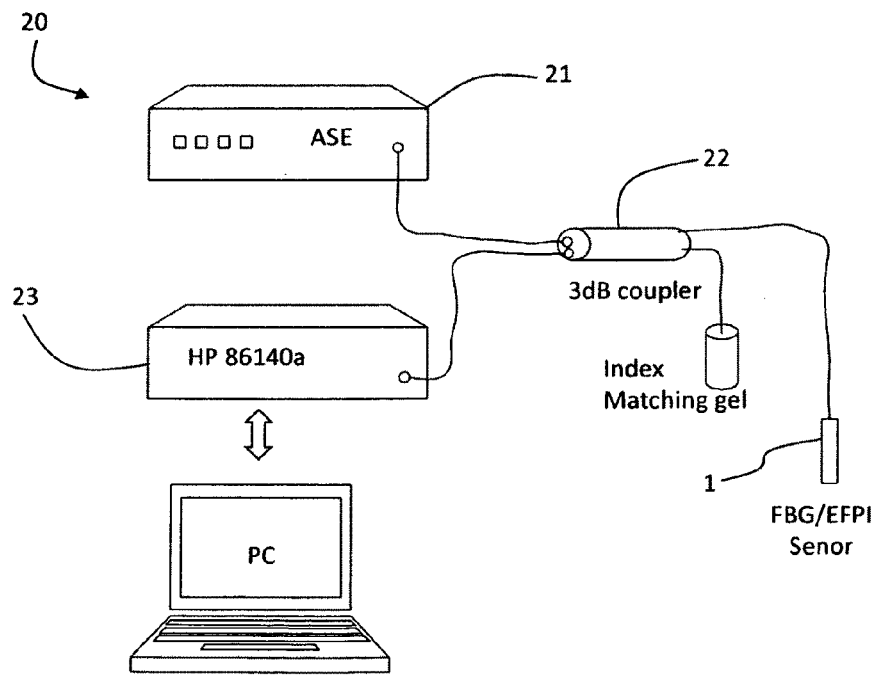
Fig. 7: Optical interrogation system

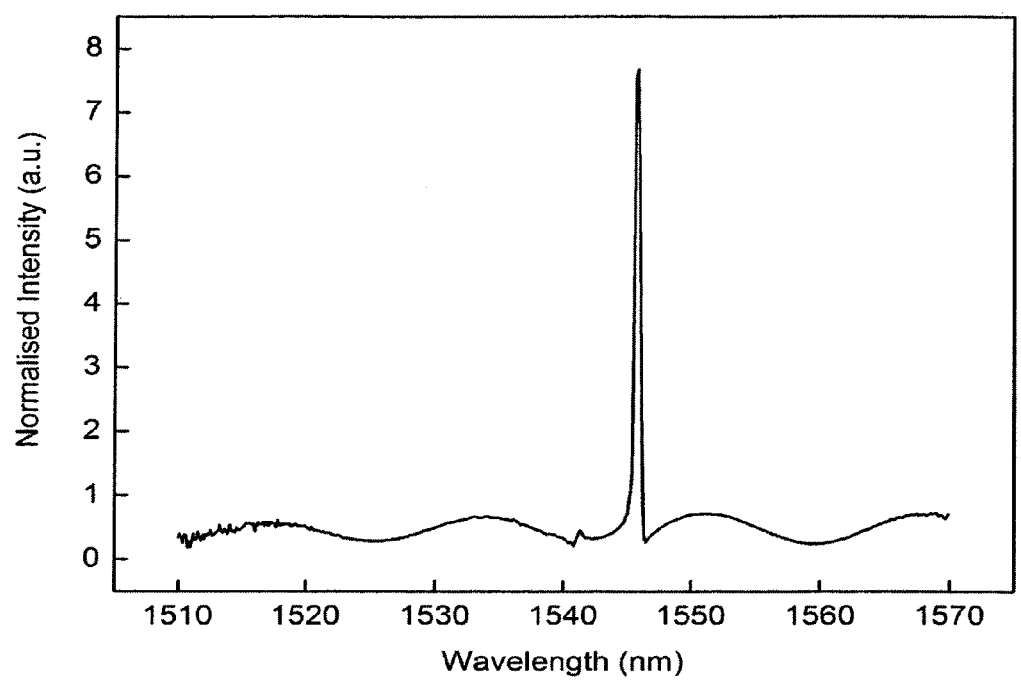
Fig. 8: Reflected spectrum of fibre optic pressure sensor

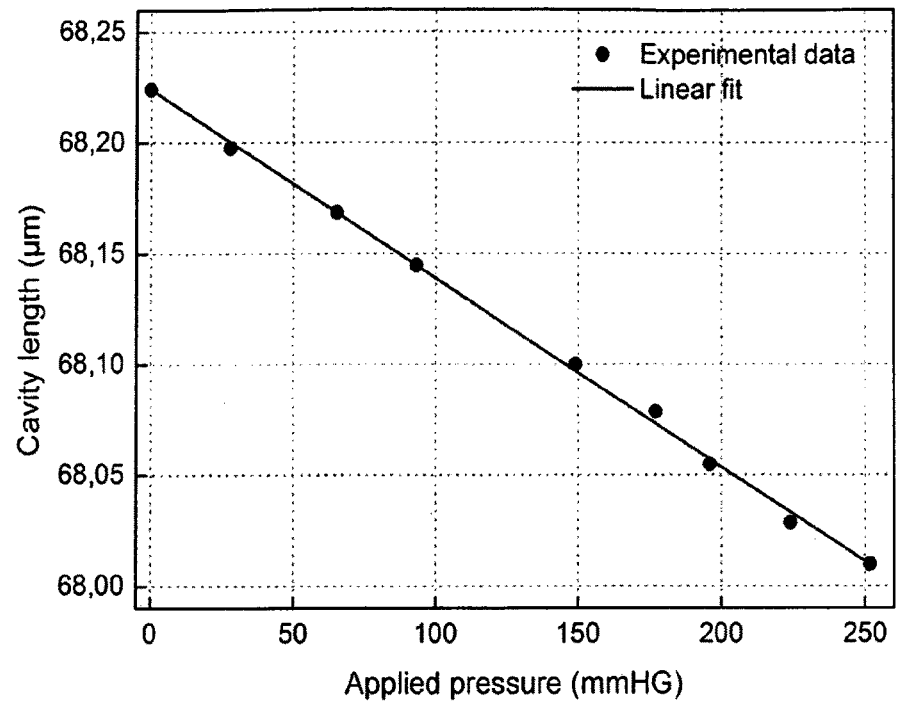
Fig. 9: Static pressure response
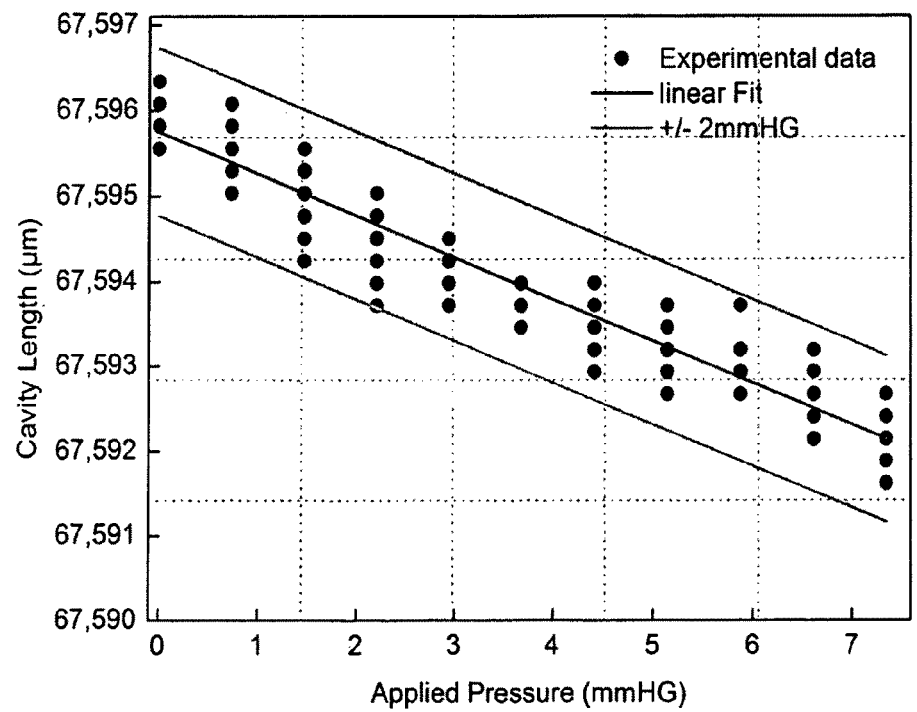
Fig. 10: Low pressure response

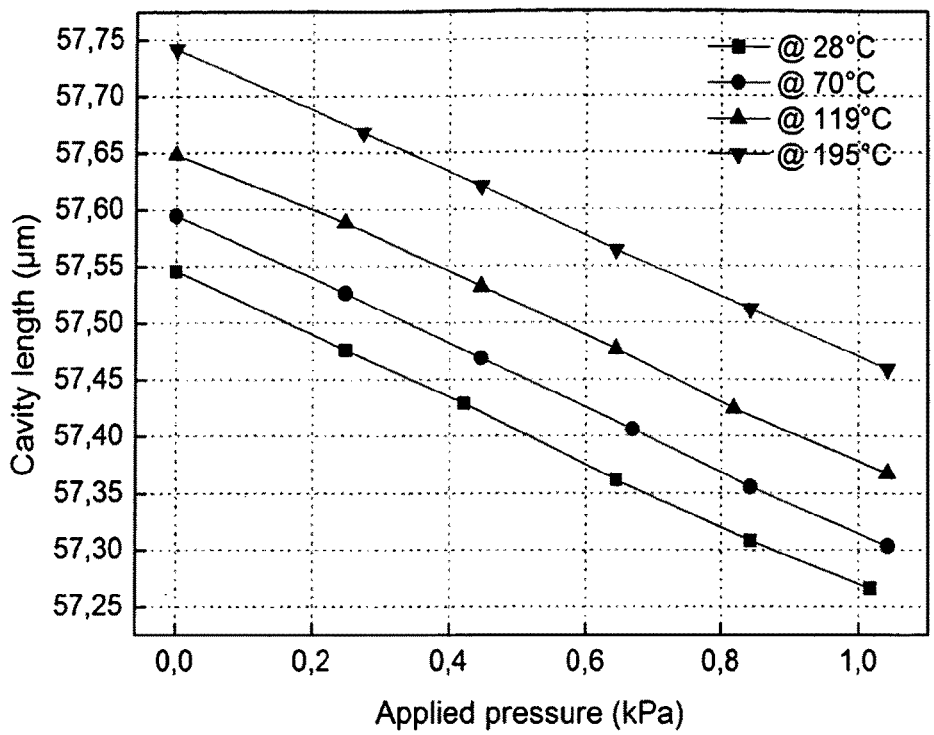
Fig. 11: Pressure response at different temperatures
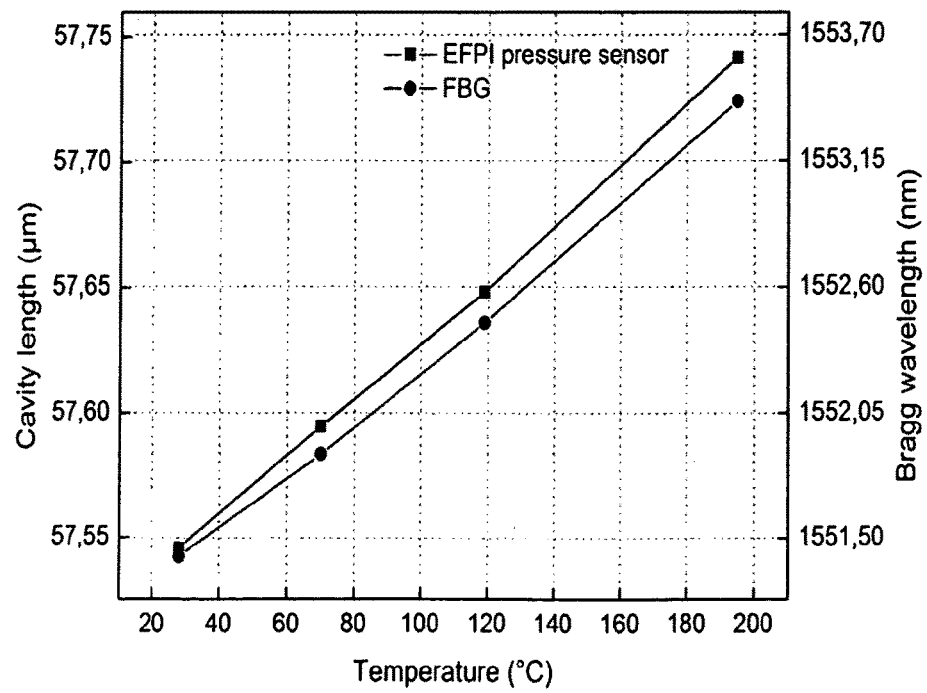
Fig. 12: Temperature response of EFPI sensor and FBG

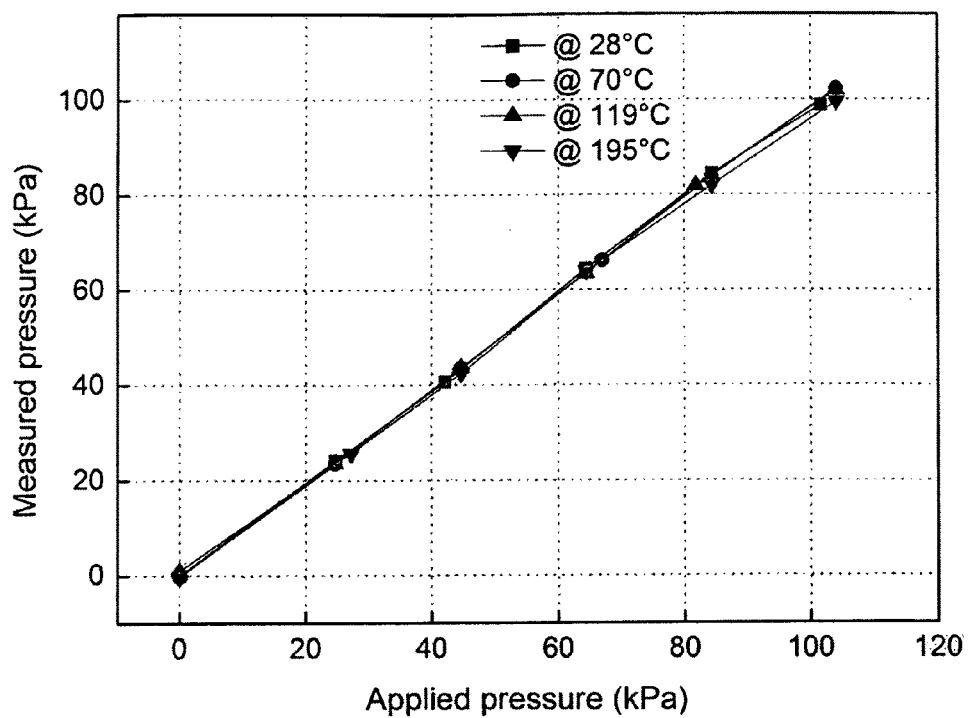
Fig. 13: Measured Pressure at different temperatures

PRESSURE SENSOR WITH AN INTERFEROMETRIC SENSOR AND AN IN-FIBER BRAGG GRATING REFERENCE SENSOR

This is a complete application claiming benefit of U.S. provisional application No. 61/282,389, filed Feb. 1, 2010.

INTRODUCTION

1. Field of the Invention

The invention relates to a pressure sensor, such as for the bio-medical field.

2. Prior Art Discussion

The references below describe various pressure sensors of the extrinsic Fabry-Perot interferometric (EFPI) type, in which applied pressure causes diaphragm deflection and therefore cavity length variation.

The invention is directed towards providing a pressure sensor with some or all of the following advantages:
  avoidance of drift, thereby enabling multi-use, and/or
  more compact, and/or
  simpler manufacturing, and/or
  reduced temperature sensitivity, and/or
  high pressure sensitivity.

REFERENCES

[1] G. C. Hill et al, "SU-8 MEMS Fabry-Perot pressure sensor", Sensors and Actuators A, vol. 138, pp. 52-62, 2007

[2] R. Wolthuis et al, "Development of medical pressure and temperature sensor employing optical spectrum modulation", IEEE Transactions on Biomedical Engineering, vol. 38, pp. 974-980, 1991

[3] R. Wolthuis et al, "Development of a dual function sensor system for measuring pressure and temperature at the tip of a single optical fiber", IEEE Transactions on Biomedical Engineering, vol. 40, pp. 298-302, 1993

[4] C. Belleville et al, "Fiber optic pressure sensor for catheter use", United States Patent Application Publication US 2006/0133715 A1

[5] E. Cibula et al, "Miniature fiber optic pressure sensor for medical application", IEEE Sensors, Orlando, Fla., USA 2002, pp. 711-714

[6] E. Cibula et al, "Miniature fiber-optic pressure sensor with a polymer diaphragm", Applied Optics, vol. 44, pp. 2736-2744, 2005

[7] K. Bremer et al, "An optical fiber micro pressure sensor with high temperature immunity", 5$^{th}$ International Symposium on Automatic Control, 18-19 Sep. 2008, Wismar, Germany 2009:

[8] K. Bremer et al, "Micro fiber optic pressure sensor based on a glass capillary and a glass diaphragm", First Asian Conference on e-Business and Telecommunication, 9-10 Feb. 2009, Changhua City, Taiwan

[9] K. Bremer et al, "Fabrication of a high temperature-resistance optical fiber micro pressure sensor", IEEE Sixth International Multi-Conference on System, Signal and Devices (SSD'09), March 23rd-26th, Djerba, Tunisia

[10] J. Xu et al, "Miniature all-silica fiber optic pressure and acoustic sensors", Optics Letters, vol. 30, pp. 3269-3271, 2005

[11] X. Wang et al, "All-fused-silica miniature optical fiber tip pressure sensor", Optics Letters, vol. 31, pp. 885-887, 2006

[12] X. Wang et al, "An Optical Fiber Tip Pressure Sensor for Medical Applications", Quantum Electronics and Laser Science Conference 2005

[13] Y. Zhu et al, "Optical Fiber Pressure and Acceleration Sensor Fabricated on a Fiber Endface", U.S. Pat. No. 7,054,011 Virginia Tech Intellectual Properties May 30, 2006

[14] D. Donlagic et al, "All-fiber high-sensitivity pressure sensor with $SiO_2$ diaphragm," Optics Letters, vol. 30, pp. 2071-2073, 2005

[15] Y. Zhu et al, "Miniature Fiber-Optic Pressure Sensor", IEEE Photonics Technology Letters, vol. 17, pp. 447-449, 2005

[16] Y. Zhu et al, "High-Temperature Fiber-Tip Pressure Sensor", IEEE Journal of Lightwave Technology, vol. 24, pp. 861-869, 2006

[17] Mario Di Giovanni, "Flat and corrugated diaphragm design handbook", *Marcel Dekker AG* 1982

[18] A. D. Kersey et al, "Fiber Grating Sensors", Journal of Lightwave Technology, vol. 15, pp. 1442-1463, 1997

[19] D. C. Abeysinghe et al, "*A novel MEMS pressure sensor fabricated on an optical fiber*", IEEE Photonics Technology Letter, vol. 13, pp. 993-995, 2001

[20] F. Shen et al, "Frequency-estimation-based signal-processing algorithm for white-light optical fiber Fabry-Perot interferometers", Applied Optics, Vol. 44, pp. 5206-5214, 2005

[21] W. Li, "Wavelength multiplexing of microelectromechanical system pressure and temperature sensors using fiber Bragg gratings and arrayed waveguide gratings", Opt. Eng., vol. 42, pp. 431-438, 2003

SUMMARY OF THE INVENTION

According to the invention, there is provided a pressure sensor comprising:
  an optical fiber having an end face,
  a diaphragm;
  a wall defining a cavity between the fiber end face and the diaphragm, the diaphragm being configured so that applied pressure causes diaphragm deflection and hence cavity length variation, and
  wherein the pressure sensor further comprises a reference sensor to cancel out temperature sensitivity.

In one embodiment, the diaphragm and the end face are arranged for interferometric sensing.

In one embodiment, the diaphragm and the end face are arranged for interferometric sensing, and wherein the interferometric sensing is of the extrinsic Fabry-Perot interferometric (EFPI) type.

In one embodiment, the reference sensor is incorporated in the optical fiber. Preferably, the reference sensor includes a Bragg Grating. Preferably, the reference sensor is an in-fiber Bragg Grating (FBG) within said optical fiber.

In one embodiment, the diaphragm thickness is set according to Fabry-Perot cavity length.

In one embodiment, the wall is in the form of a capillary within which the optical fiber is inserted, and preferably the capillary is of glass material.

In one embodiment, the wall is in the form of a glass capillary within which the optical fiber is inserted, and wherein the diaphragm and the optical fibre are of glass material.

In one embodiment, the wall is in the form of a glass capillary within which the optical fiber is inserted, and wherein the diaphragm and the optical fibre are of glass material, and wherein the optical fiber and the diaphragm are secured to the capillary by a fusion splice.

In one embodiment, the wall is in the form of a glass capillary within which the optical fiber is inserted, and wherein the diaphragm and the optical fibre are of glass material, and wherein the optical fiber and the diaphragm are secured to the capillary by a fusion splice, and wherein the reference sensor is contained within the fiber, and wherein the fiber is located such that reflections from the fiber end face, and from the diaphragm are propagated in the same direction back along the fiber.

In another aspect, the invention provides a medical device incorporating a pressure sensor as defined above in any embodiment. The device may be a catheter.

In another aspect, the invention provides a method of manufacturing a pressure sensor comprising an optical fiber having an end face, a capillary into which the fibre is inserted, a diaphragm secured to the capillary, the capillary defining a cavity between the fiber end face and the diaphragm, the diaphragm being configured so that applied pressure causes diaphragm deflection and hence cavity length variation, and a reference sensor incorporated in the optical fiber to cancel out temperature sensitivity, the method comprising the step of controlling cavity length by fiber alignment within the capillary with respect to the diaphragm.

In one embodiment, said alignment is performed using a broadband source, an optical coupler or circulator, and an optical spectrum analyser.

In one embodiment, the diaphragm is manufactured by splicing an optical fibre to the capillary and reducing length of the fiber until it reaches a desired diaphragm thickness.

In one embodiment, the diaphragm is manufactured by splicing an optical fibre to the capillary and reducing length of the fiber until it reaches a desired diaphragm thickness, and wherein the thickness is reduced at least in part by etching, and wherein there is dynamic control of etching according to measured cavity length.

In one embodiment, in the diaphragm is manufactured by splicing an optical fibre to the capillary and reducing length of the fiber until it reaches a desired diaphragm thickness, and wherein the thickness is reduced at least in part by etching, and wherein there is dynamic control of etching according to measured cavity length, and wherein said measurement is performed using an optical interrogation system.

DETAILED DESCRIPTION OF THE INVENTION

The invention will be more clearly understood from the following description of some embodiments thereof, given by way of example only with reference to the accompanying drawings in which:—

FIGS. 2 and 3 are diagrams showing fabrication of an EFPI cavity and a glass diaphragm respectively;

FIGS. 4 and 5 are images showing a pressure sensor before etching and a glass diaphragm surface after etching;

FIG. 6 is a plot showing change of EFPI cavity length during etching;

FIG. 7 shows an optical interrogation system incorporating a pressure sensor of the invention;

FIG. 8 is an intensity vs. wavelength plot showing reflected spectrum of the pressure sensor;

FIGS. 9 to 11 are plots showing cavity length vs. applied pressure in various tests, the applied pressure for the FIG. 9 test being static, for the FIG. 10 plot being low pressure and for the FIG. 11 test being at different temperatures;

FIG. 12 is a plot showing temperature response, and

FIG. 13 is a plot showing measured pressure at different temperatures.

DESCRIPTION OF THE EMBODIMENTS

Overview

Figure 1:
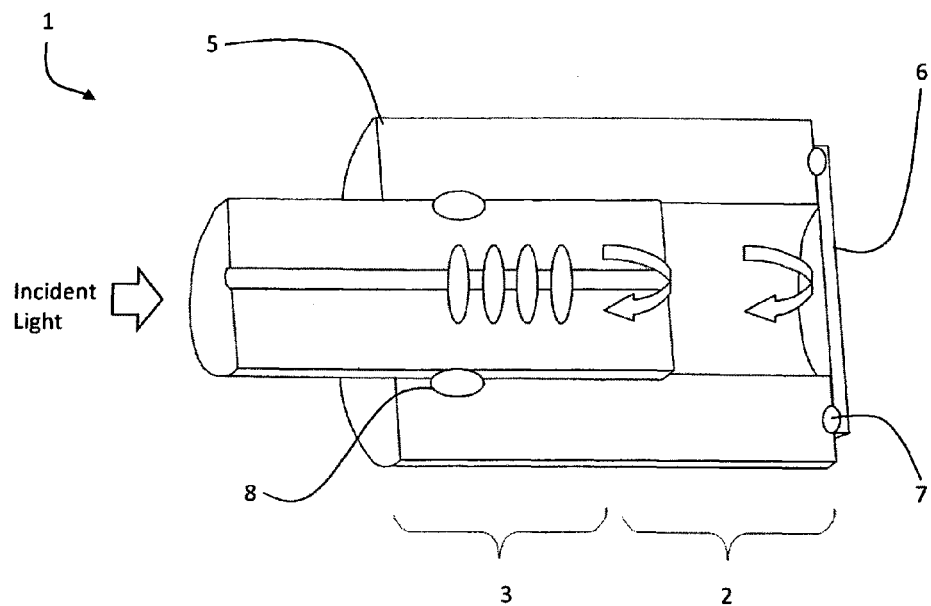
FIG. 1 is a diagrammatic cross-sectional view of a pressure sensor of the invention.

Referring to FIG. 1 a pressure sensor 1 for medical applications comprises a silica optical fiber extrinsic Fabry-Perot interferometric (EFPI) pressure sensor 2 and an in-fiber Bragg grating (FBG) 3. The cavity of the EFPI pressure sensor 2 is formed by the endface of the FBG, a glass capillary 5 and a glass diaphragm 6. The glass diaphragm 6 is secured in place by a fusion splice 7 and the glass capillary 5 by a fusion splice 8. As illustrated, incident light is directed into the FBG 3 and there are reflections in the EFPI pressure sensor 2.

Applied pressure causes a deflection of the glass diaphragm 6 and hence modulation of the EFPI sensor 2 cavity. The FBG 3 is used as a reference sensor to eliminate temperature cross-sensitivity of the EFPI pressure sensor 2.

Manufacture of Pressure Sensor.

The EFPI cavity was fabricated using a 200 µm silica glass fiber, a 133/220 µm (inner/outer diameter) silica glass capillary and a standard telecommunication FBG.

Figure 2:
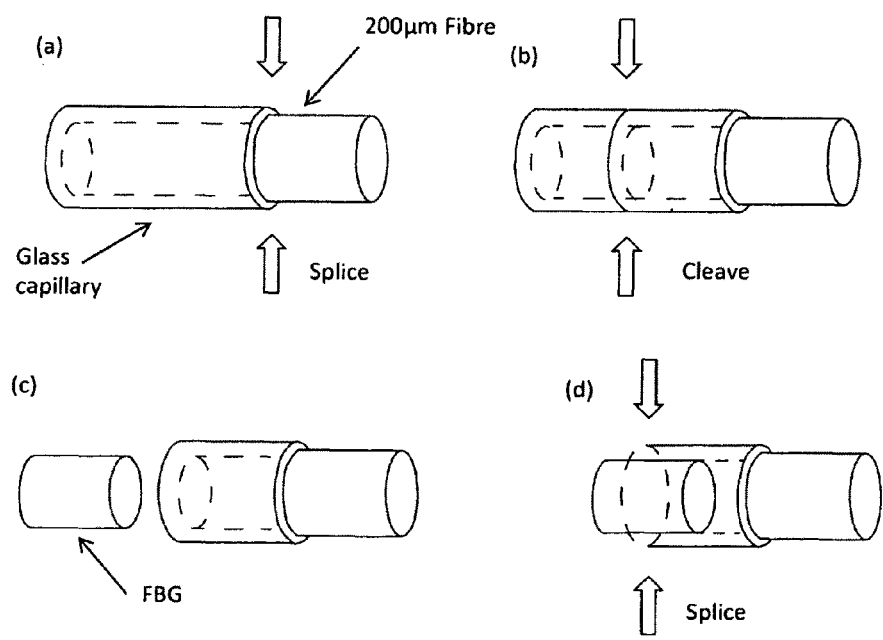

Initially, the end faces of the 200 µm silica glass fiber and the silica glass capillary were polished using 12 µm, 3 µm, 1 µm and 0.5 µm lapping films and carefully cleaned to obtain planar surfaces. As shown in FIG. 2, both planar surfaces were spliced together using a fusion splicer—step (a) of FIG. 2. Then the silica glass capillary was cleaved 5 mm away form the capillary/200 µm fiber splice—step (b) of FIG. 2. After that, the FBG 3 was inserted into the silica glass capillary 5 and both elements were bonded together using the fusion splicer again. The fusion splice was placed 4 mm away form the capillary/200 µm fiber fusion splice—step (c) and (d) of FIG. 2. The EFPI cavity length can be controlled precisely due to the high resolution fiber alignment of the fusion splicer and an optical control system comprising a broadband source (BBS), an optical coupler or circulator and an optical spectrum analyser (OSA).

The silica glass diaphragm 6 was then fabricated, as shown in FIG. 3, using the 200 µm silica glass fiber which was cleaved 200 µm away from the splicing point—step (a) of FIG. 3. Following this step, the remaining structure was clamped into an SMA connector, in this embodiment a 200/230 µm steel SMA connector, and the 200 µm silica glass fiber was polished to a thickness of 10 µm using 12 µm, 3 µm, 1 µm and 0.5 µm diamond lapping films—step (b) of FIG. 3. In order to achieve high degree of pressure sensitivity, the glass diaphragm must be very thin. Therefore, the diaphragm was then wet etched of four to two microns, depending on the required pressure sensitivity, using HF acid—step (c) of FIG. 3. Two examples of a fiber optic pressure sensor before and a diaphragm surface after etching are shown in FIG. 4 and FIG. 5.

The diaphragm thickness was controlled online during etching by calculating the EFPI cavity length using an optical interrogation system 20, as shown in FIG. 7. As described in Equation (2) below, the deflection of the silica glass diaphragm and hence the decay of the EFPI cavity length increases for a thinner diaphragm. Accordingly this information is used to control the etching process of the glass diaphragm 6. An example of a modulated EFPI cavity length during etching is shown in FIG. 6.

The decrease of the diaphragm 6 thickness during etching causes sinusoidal oscillations and a decay of the EFPI 2 cavity length. The sinusoidal oscillations are due to the second and third cosine term of Equation (1) below. The decay is derived form the deflection of the glass diaphragm.

The fiber optic pressure sensor 1 was interrogated using a system 20 shown in FIG. 7. Light form an ASE broadband source 21 was coupled via a 3 dB-coupler 22 into the sensor 1 and the output spectrum was reflected back towards an OSA (HP86140A) 23. The OSA 23 captured the reflected output spectrum and a computer was utilized to acquire the applied pressure and temperature respectively. An example of a reflected output spectrum for a fiber optic based pressure sensor 1 for medical application with an EFPI cavity length of $L_C$=68 µm, a silica glass diaphragm thickness of d=2 µm and a Bragg wavelength of $\lambda_B$=1545.8 nm is shown in FIG. 8. The reflected output spectrum of the EFPI pressure sensor 2 is similar to a sinusoidal wave, whereas the output of the FBG sensor 3 has a narrow bandwidth with a high reflectivity.

The cavity length $L_C$ of the EFPI pressure sensor is measured from the sinusoidal wave of the reflected spectrum as:

$$L_C = \frac{\Delta\varphi \cdot \lambda_1 \lambda_2}{4\pi(\lambda_2 - \lambda_1)} \quad (7)$$

In Equation (7), $\lambda_1$ and $\lambda_2$ are two wavelengths that are $\Delta\phi$ out of phase. The shift of the Bragg wavelength $\Delta\lambda_B$ was measured by correlating the normalized output spectrum with the known spectrum of the FBG.

Method of Operation

As illustrated in FIG. 1, the incident light is reflected within the EFPI pressure sensor 2 at the end face of the FBG 3 and at the inside and outside surface of the glass diaphragm. All three reflections propagate back through the same fiber and generate interference fringes which are given by [15]:

$$I(\lambda, L) = A_1^2 + A_2^2 + A_3^2 - 2A_1A_2\cos\left(\frac{4\pi L_C}{\lambda}\right) + 2A_3A_1\cos\left(\frac{4\pi(L_C + nd)}{\lambda}\right) - 2A_2A_3\cos\left(\frac{4\pi nd}{\lambda}\right) \quad (1)$$

In Equation (1) the first and second cosine terms describes the interference between the end face of the FBG 3 and the inner surface and the outer surface of the diaphragm respectively. The third cosine term is the interference between the inner and outer surface of the diaphragm 6. $A_1$, $A_2$ and $A_3$ are the amplitudes of the reflected light at the endface of the FBG 3 and the inside and outside surface of the diaphragm 6. n is the refractive index of silica. $L_C$ is the length of the air cavity between the endface of the FBG 3 and the inside surface of the diaphragm, d is the thickness of the diaphragm and $\lambda$ is the optical wavelength. The length $L_C$ of the air cavity changes with the deflection of the diaphragm as a result of a pressure difference between the inside and outside surfaces of the diaphragm. The changes in the length of the air cavity: $\Delta L_P$ due to the static pressure difference $\Delta P$ at the centre of the diaphragm may be expressed as [17]:

$$\Delta L_P = \frac{3(1 - \mu^2)}{16Eh^3} \cdot a^4 \cdot \Delta P = a_{21}\Delta P \quad (2)$$

In Equation (2), r is the radius of the diaphragm, E is Young's Modulus, µ the Poisson's Ratio. It follows from Equation (2) that the deflection of the diaphragm depends linearly on the pressure difference $\Delta P$. Hence the phase of the first and second cosine term of Equation (2) will also depends linearly on the pressure difference $\Delta P$.

The thermal cross-sensitivity of the EFPI pressure sensor is caused by the thermal expansion of all glass components and the air within the EFPI cavity. It can be derived as follows:

$$\Delta L_T = \left(L_S(\alpha_C - \alpha_{SM}) + L_C\alpha_{SM} + \frac{P_S}{T_S}\right)\Delta T = a_{22}\Delta T \quad (3)$$

In Equation (3), $L_S$ is the distance between glass diaphragm and FBG/capillary fusion splice, $\alpha_C$ and $\alpha_{SM}$ are the coefficients of thermal expansion (CTE) of the silica glass capillary 5 and FBG 3 fiber respectively. $P_S$ and $T_S$ are the pressure and temperature during sealing and S is the pressure sensitivity of the EFPI pressure sensor 2.

FBGs are simple, intrinsic sensing elements which have been extensively used for strain, temperature and pressure sensing. The grating is formed as a regular variation in the refractive index of the core of a single-mode (SM) optical fiber. In normal operation this causes light propagating in the optical SM fiber core of a particular wavelength (the Bragg wavelength $\lambda_B$) to be reflected back. The Bragg wavelength is defined as [18]:

$$\lambda_B = 2n_{eff}\Lambda \quad (4)$$

where $n_{eff}$ is the refractive index of the core material and $\Lambda$ is the period of the grating. All other wavelengths are transmitted in the normal manner through the fiber. The sensing function of an FBG derives from the sensitivity of the refractive index and grating period to externally applied mechanical or thermal perturbation. It is experienced by the FBG through altering the reflected Bragg wavelength $\lambda_B$.

In the fiber optic pressure sensor 1 of the invention the FBG 3 is fully encapsulated in the glass capillary 5. This keeps the FBG strain and pressure free and hence it is only sensitive to temperature. The temperature sensitivity occurs through the effect on the induced refractive index change and on the thermal expansion coefficient of the SM fiber. The Bragg wavelength shift $\Delta\lambda_{B,T}$ due to temperature change $\Delta T$ is given by [18]:

$$\Delta\lambda_{B,T} = \lambda_B\left(\alpha + \frac{1}{n_{eff}}\frac{dn_{eff}}{dT}\right)\Delta T = a_{12}\Delta T \quad (5)$$

where $dn_{eff}/dT$ is the thermo optic coefficient.

Using the temperature and pressure coefficients from both sensing units a matrix can be constructed as:

$$\begin{bmatrix} \Delta\lambda_B \\ \Delta L_C \end{bmatrix} = \begin{bmatrix} 0 & a_{12} \\ -a_{12} & a_{22} \end{bmatrix}\begin{bmatrix} \Delta P \\ \Delta T \end{bmatrix} \quad (6)$$

This linear approximation of the FBG is only valid for relatively low temperatures.

The inversion of the matrix can be used to discriminate between the pressure $\Delta P$ and temperature $\Delta T$ information from the FBG and EFPI pressure sensors 3 and 2 respectively.

The fiber optic pressure sensor 1 has an EFPI cavity length of $L_C$=68 µm, a silica glass diaphragm 6 thickness of d=2 µm. A Bragg wavelength of $\lambda_B$=1545.8 nm was used to evaluate the low pressure response in the tests below.

Tests

The fiber optic based pressure sensor 1 was placed into a pressure chamber and measurements were started at atmospheric pressure (labelled with 0 mmHG) and increased to 251 mmHG (33.5 kPa). The temperature was constant during the experiment. As shown in FIG. 9, at an applied pressure of $\Delta P=251$ mmHG a change $\Delta L_C=210$ nm of the EFPI cavity length was observed.

The low pressure resolution of the fiber optic based pressure sensor used above is shown in FIG. 10. The pressure response was tested by adjusting the pressure sensor in a water column and analysing the reflected output spectrum. The Measurement was started at atmospheric pressure (labelled with 0 mmHG) and increased to 7.3 mmHG with an increment of 0.73 mmHg, which is equal to 1 cmH$_2$O. As shown in FIG. 10, a pressure resolution of +/−2 mmHG was achieved.

The discrimination between pressure and temperature was evaluated by measuring the pressure response at different temperatures. At first a fiber optic based pressure sensor was mounted to a high temperature resistance pressure chamber and the whole arrangement was placed into an electric furnace. For this measurement a fiber optic pressure sensor with an EFPI cavity length of $L_C=57.55$ µm, a silica glass diaphragm thickness of $d=2.6$ µm and a Bragg wavelength of $\lambda_B=1551.42$ nm was used. Pressure measurements were start at atmospheric pressure (labelled with 0 kPa) and increased to 100 kPa for four different temperatures (28° C., 70° C., 119° C., 195° C.). The pressure response of the EFPI pressure sensor for different temperatures and the temperature responses for the EFPI pressure sensor and the FBG are shown in FIG. 11 and FIG. 12 respectively.

The pressure and temperature coefficients of the FBG and EFPI pressure sensor were calculated to be 11.85 pm/K (FBG) and 2.78 nm/kPa; 1.13 nm/K (EFPI pressure sensor). Therefore a pressure error reading of 0.4 kPa/K (3 mmHG/K) is caused by the temperature coefficient of the EFPI pressure sensor, as shown in FIG. 12.

Using the temperature and pressure coefficients from both sensing units the matrix form Equation (6) can be constructed as:

$$\begin{bmatrix} \Delta \lambda_B \\ \Delta L \end{bmatrix} = \begin{bmatrix} 0 & 11.85 \text{ pm/K} \\ -278 \text{ nm/kPa} & 1.13 \text{ nm/K} \end{bmatrix} \begin{bmatrix} \Delta P \\ \Delta T \end{bmatrix} \quad (7)$$

The inversion of the matrix is used to distinguish between pressure $\Delta P$ and temperature $\Delta T$ at the point of measurement. As shown in FIG. 13, the results of the reversed matrix demonstrate a good correlation between the measured and applied pressure for all temperatures.

It will be appreciated that the invention provides for very effective fabrication of a pressure sensor and as is demonstrated above it can perform as a high pressure sensitive fiber optic based pressure sensor for medical applications. Its all-silica structure, miniature size (220 µm diameter and 5 mm long) and high pressure sensitivity makes the pressure sensor suitable for medical uses. Moreover, the encapsulated FBG 3 facilitates discrimination between pressure and temperature readings at the point of measurement.

Further improvements of the fabrication process are possible to increase the pressure sensitivity. For example, the deflection of the silica glass diaphragm 6 can be increased by using a silica glass capillary 5 with a larger inner diameter. Sputtering a thin metal or dielectric coating onto the FBG endface and outer surface of the diaphragm 6 will increase their reflectance and hence the pressure sensitivity of the fiber optic based pressure sensor. The surface of the outer diaphragm can be altered to a corrugated structure to reduce the stiffness of the silica glass diaphragm by using, for example, focused ion beam milling (FIB).

Instead of the glass diaphragm 6 a thin silicon wafer or a whole MEMS pressure chip [19] can be bonded onto the silica glass capillary 5 using, for example, anodic boding. This may increase the flexibility of diaphragm diameter and thickness during fabrication and it still has the advantage of simultaneous pressure and temperature readings at the point of measurement due to the encapsulated FBG 3 inside the silica glass capillary.

Improved cost-efficiency can be obtained by using a coherence division multiplexing technique [20], or a wavelength division multiplexing (WDM) [21] technique as it requires only one optical interrogation system to read out several fiber optic pressure sensors.

It will be appreciated that the combination of an all-fused silica optical fiber EFPI pressure sensor and an FBG 3 retains the advantages of an all-glass structure, is miniature size (220 µm outer diameter), exhibits high pressure sensitivity and low hysteresis, and facilitates the discrimination of pressure and temperature readings at the point of measurement. The inexpensive and simple fabrication method allows production of a low-cost, disposable medical device. Furthermore, the on-line etching control of the glass diaphragm 6 provides the opportunity to achieve high pressure sensitivity and good fabrication repeatability.

The miniature construction makes the fiber optic pressure sensor highly compatible with insertion into a wide range of catheters, including oesophageal, urethral, and vascular catheters. The sensor also reduces the risk of inflammation or infection (when disposable) and facilitates precise spatial and temporal resolution measurements in targeted critical regions.

Moreover, the all fused silica glass structure is fully biocompatible. There is little risk of leakage of materials by for example leaching from epoxies.

Furthermore, because the sensor is fabricated from non-ferrous materials means that it can be used in specialised environments such as inside MRI scanners without distorting the image or causing any discomfort to the patient.

The invention is not limited to the embodiments described but may be varied in construction and detail.

The invention claimed is:

1. A pressure sensor comprising:
    an optical fiber having an end face,
    a diaphragm; and
    a wall defining a cavity between the fiber end face and the diaphragm, the diaphragm being configured so that applied pressure causes diaphragm deflection and hence cavity length variation,
    wherein the pressure sensor further comprises a reference sensor to compensate temperature sensitivity,
    wherein the diaphragm and the end face are arranged for interoferometric sensing; and
    wherein the reference sensor is an in-fiber Bragg Grating (FBG) within said optical fiber.

2. The pressure sensor as claimed in claim 1, wherein the interferometric sensing is of the extrinsic Fabry-Perot interferometric (EFPI) type.

3. The pressure sensor as claimed in claim 1, wherein the wall is in the form of a capillary within which the optical fiber is inserted.

4. The pressure sensor as claimed in claim 1, wherein the wall is in the form of a glass capillary within which the optical fiber is inserted.

5. The pressure sensor as claimed in claim 1, wherein the wall is in the form of a glass capillary within which the optical fiber is inserted, and wherein the diaphragm and the optical fibre are of glass material.

6. The pressure sensor as claimed in claim 1, wherein the wall is in the form of a glass capillary within which the optical fiber is inserted, and wherein the diaphragm and the optical fibre are of glass material, and wherein the optical fiber and the diaphragm are secured to the capillary by a fusion splice.

7. The pressure sensor as claimed in claim 1, wherein the wall is in the form of a glass capillary within which the optical fiber is inserted, and wherein the diaphragm and the optical fibre are of glass material, and wherein the optical fiber and the diaphragm are secured to the capillary by a fusion splice, and wherein the reference sensor is contained within the fiber, and wherein the fiber is located such that reflections from the fiber end face, and from the diaphragm are propagated in the same direction back along the fiber.

8. A medical device incorporating a pressure sensor comprising:
- an optical fiber having an end face,
- a diaphragm; and
- a wall defining a cavity between the fiber end face and the diaphragm, the diaphragm being configured so that applied pressure causes diaphragm deflection and hence cavity length variation,
- wherein the pressure sensor further comprises a reference sensor to compensate temperature sensitivity, and
- wherein the diaphragm and the end face are arranged for interoferometric sensing;
- wherein the reference sensor is an in-fiber Bragg Grating (FBG) within said optical fiber.

9. The medical device as claimed in claim 8, wherein the device is a catheter or part thereof.

\* \* \* \* \*